United States Patent [19]

Franz et al.

[11] 4,367,362

[45] Jan. 4, 1983

[54] PROCESS FOR THE ISOMERIZATION OF N-ALKENES

[75] Inventors: Gerhard Franz; Friedrich Heinrich; Hans-Josef Ratajczak, all of Marl, Fed. Rep. of Germany

[73] Assignee: Chemische Werke Huels, Aktiengesellschaft, Marl, Fed. Rep. of Germany

[21] Appl. No.: 224,235

[22] Filed: Jan. 12, 1981

[30] Foreign Application Priority Data

Jan. 10, 1980 [DE] Fed. Rep. of Germany ....... 3000650
Oct. 29, 1980 [DE] Fed. Rep. of Germany ....... 3040698

[51] Int. Cl.$^3$ .............................................. C07C 5/27
[52] U.S. Cl. .................................... 585/671; 585/668; 585/669
[58] Field of Search ........................ 585/671, 669, 668

[56] References Cited

U.S. PATENT DOCUMENTS

| | | | |
|---|---|---|---|
| 2,471,647 | 5/1949 | Oblad et al. | 585/671 |
| 3,069,362 | 12/1962 | Mays et al. | 252/419 |
| 3,558,734 | 1/1971 | Myers | 585/671 |
| 4,038,337 | 7/1977 | Manara et al. | |

FOREIGN PATENT DOCUMENTS

| | | | |
|---|---|---|---|
| 1065005 | 4/1967 | United Kingdom | 585/671 |
| 1065006 | 4/1967 | United Kingdom | 585/671 |
| 1065007 | 4/1967 | United Kingdom | 585/671 |

*Primary Examiner*—Delbert E. Gantz
*Assistant Examiner*—A. Pal
*Attorney, Agent, or Firm*—Millen & White

[57] ABSTRACT

A process for the catalytic skeleton isomerization of n-alkenes to isoalkenes comprises contacting the n-alkene with a fluorinated aluminum oxide as the catalyst at temperatures of 250°–550° C., in the presence of 0.5–150% by weight of water, based on the weight of the alkene employed and replenishing the fluorine discharged from the catalyst in metered amounts, continuously or discontinuously, using, e.g., a volatile fluorine compound. The catalyst, partially deactivated by coking, is regenerated by burning it off with an oxygen-containing gas in the presence of steam.

13 Claims, 3 Drawing Figures

PROCESS FOR THE ISOMERIZATION OF N-ALKENES

BACKGROUND OF THE INVENTION

The present invention relates to a process for the skeleton isomerization of n-alkenes to isoalkenes, i.e., for the conversion of unbranched hydrocarbons into branched, unsaturated hydrocarbons.

The demand for isoalkenes, especially in the $C_4$- to $C_5$-range, has risen considerably in recent years due to the development of new techniques, a change in the raw material situation, and legal requirements enacted in the fuel sector. Examples of the new developments are the methyl tert-butyl ether synthesis, which is a simple processing technique for the $C_4$-cut with the simultaneous production of a valuable fuel component; and processes for the manufacture of methyl methacrylate, starting with isobutene or tert-butanol.

The skeleton isomerization of n-alkenes to isoalkenes is a conventional reaction. The conversion is normally conducted as a heterogeneously catalyzed gas-phase reaction in the temperature range of 300° to 600° C. Catalysts employed are acidic solids, e.g., aluminum oxides acidified by suitable promoters. The aluminum oxide is preferably utilized in the $\eta$- or $\gamma$-modification.

However, problems are encountered in the rapid, extensive coking of the catalyst which ensues, resulting in very brief periods of operation in between the necessary frequent regenerations. For example, during the isomerization of n-butane to isobutane, carried out on an extremely large scale under practical conditions, the catalyst is even doped with Pd or Pt, and hydrogen is added to the hydrocarbon mixture, so that the olefins produced in secondary reactions can be hydrogenated as quickly as possible again to alkanes. Without such measures, the period of usefulness for the catalyst drops from about ½ year to a few days, because the olefins lead to rapid coke formation on the catalyst. For this reason the heretofore known processes for butene isomerization have not as yet been employed on an industrial scale.

For example, DAS [German Published Application] No. 1,518,580 describes a process for butene isomerization wherein the conversion is conducted in the presence of an aluminum oxide which contains 0.5–1.5% by weight of fluorine at 250°–550° C. The short lifetime of the catalyst is a disadvantage in this method. As a consequence of coke deposits, the activity is considerably reduced within only a few hours. Moreover, for regeneration purposes, the catalyst must be burnt off with air.

DOS [German Unexamined Laid-Open Application] No. 2,534,459 describes a process wherein the alkene is brought into contact with a catalyst obtained by reacting an activated aluminum oxide with an ester of silicic acid. The results of ths process are that, here again, periodic regenerations are required at intervals of 10–20 hours.

Furthermore, from DAS No. 1,518,584 it is known to conduct the isomerization in the presence of hydrogen as a diluent gas as a measure for prolonging the useful life of a fluorinated aluminum oxide catalyst. The half-life of the catalyst, defined as the point at which the percentage content of isobutene, based on the total butene in the gaseous product, has dropped to half its equilibrium value at 450° C., is disclosed as 69 hours. When using inert gases, such as $H_2$ or $N_2$, however, the separation of the inert compounds from the $C_4$-hydrocarbons is expensive since this normally requires the use of refrigeration. Furthermore, additional safety measures are required in the necessary regeneration procedure to avoid the occurrence of explosive gaseous mixtures.

SUMMARY OF THE INVENTION

Therefore, it is an object of the present invention to provide a process for the isomerization of n-alkenes to isoalkenes which is distinguished by prolonged catalyst operating periods, i.e., the operating time between two regenerations, and by an attendant simple procedure for catalyst regeneration.

Upon further study of the specification and appended claims, further objects and advantages of this invention will become apparent to those skilled in the art.

These objects have been attained by providing a process for the catalytic skeleton isomerization of n-alkenes to isoalkenes comprising contacting the n-alkene with a fluorinated aluminum oxide as the catalyst at temperatures of 250°–550° C., in the presence of 0.5–150% by weight of water, based on the weight of the alkene employed and replenishing the fluorine discharged from the catalyst in metered amounts, continuously or discontinuously, using, e.g., a volatile fluorine compound. The catalyst, partially deactivated by coking, is regenerated by burning it off with an oxygen-containing gas in the presence of steam.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DISCUSSION

Figure 1:
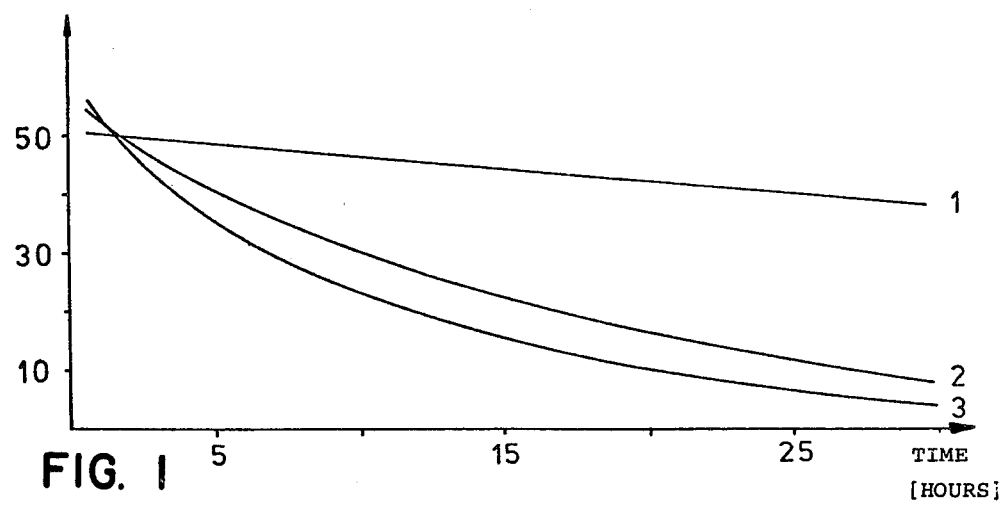
FIGS. 1–3, respectively, display graphs of conversion(%), isobutene yield(%) and isobutene selectivity(%) as a function of reaction time (hrs.) for: 1. the invention using a $H_2O$ component; 2. the conventional reaction using $H_2$ as inert gas; and 3. the conventional reaction without water and an inert gas.

Surprisingly, the expedient of including 0.5–150% by weight of water, based on the n-alkene feed, contrary to expectations, neither completely deactivates the catalyst nor damages it irreversibly. Rather, a uniform activity is obtained which is maintained even over very long periods of time and brings with it a high selectivity in the resultant isomerization to the isoalkenes, for example to isobutene.

That is, contrary to all expectations, the fluorine is not spontaneously discharged as HF by the large amounts of water. For example, chlorine in reforming catalysts is rapidly discharged even by small quantities of water. Nevertheless, the fluorine in the catalyst of the invention's process is discharged only to a quite minor extent even by large amounts of water. In the aqueous phase downstream of the reactor, only a few ppm of fluorine are detected. A gradual damage to the catalyst is observable only after several days of operation.

However, even this gradual damage is entirely avoided by replacing the small amount of fluorine discharged from the catalyst by adding a volatile fluorine compound to the feed mixture, for example HF. It is possible to add HF to the fresh water in concentration corresponding to the discharged fluorine which can be determined by conventional procedures. In the simplest case, the water of reaction is recirculated, optionally after a filtering step.

The supplemental fluorination of the catalyst can also be effected by adding organic fluorine compounds, such as, for example, carbon tetrafluoride or fluoroform. Generally, any fluorine compound can be employed as long as it is otherwise inert in the reaction and results in a replenishment of the discharged fluorine in the catalyst. These compounds are likewise added to the feed mixture in metered amounts corresponding to the fluorine effluent. Basically, the supplemental fluorination can be effected continuously, in accordance with the F discharge rate, or discontinously. Further advantageously, the discharged fluorine is recovered exclusively in the water phase. The formation of organofluorine compounds is not observed.

As mentioned, by adding 0.5–150% by weight of water to the feed olefin, the operating period between required regenerations due to the partial coking of the catalyst can be substantially prolonged, e.g., operational times of 5–100 days. This regeneration of the catalyst partially deactivated by coking takes place by burning it off with an oxygen (i.e., $O_2$)-containing gas in the presence of steam. As compared with the mode of operation without water and/or with the addition of equimolar amounts of nitrogen or hydrogen, the half-life, can be raised by a factor of 10 or above, with a comparable initial conversion. Deactivation can even be entirely avoided by adding larger amounts of water, if constant, though lower conversion rates are acceptable. The suitable amounts of water are in the range of 0.5 to 150% by weight, preferably 2–130% by weight, based on the amount of alkene employed. Amounts of water above 150% by weight do not produce any further improvement or result in conversions which are so small that they are no longer of technical interest. For water quantities below 0.5% by weight, the desired effect is too slight.

In addition to prolonging the half-life, the addition of water furthermore produces an increase in selectivity to values of, e.g., 70–94%. This is due to a reduction in cracking products, as well as, in particular, aromatics and oligomeric products. Both of these secondary reactions are surely critically responsible for the coking of the catalyst. For example, the amounts of these products which are produced can be observed to vary in inverse correlation with the half-life value.

Suitable n-alkenes for use in the process of this invention include butene-1, butene-2, n-pentenes, as well as alkenes of 6 to 16 carbon atoms. Preferably, $C_4$-n-alkenes are utilized, such as butene-1 and butene-2.

In conducting the present invention, an alkene or an alkene mixture, optionally also in the presence of alkanes or other inert gases such as nitrogen or $CO_2$, can be homogenized with steam and passed over fluorinated aluminum oxides at temperatures of 250°–550° C. preferably 350°–500° C. The fluorinated aluminum oxides are conventional and can be produced according to the prior art, e.g., DAS No. 1,518,580, whose disclosure is incorporated by reference herein.

The reaction can be conducted in a fixed bed as well as in a fluidized bed. The reaction pressure generally ranges from atmospheric pressure to 10 bar. However, it is also possible to operate under a vacuum. When operating under pressure, larger amounts of water must be utilized than under normal pressure, for example, 25–150% by weight at a pressure of 6 bar. In general, when working under pressure, preferably at 3–7 bar, it is preferred to use 51–150% by weight of water, especially 55–130% by weight of water.

The space throughput velocity, expressed as LHSV (liquid hourly space velocity) ranges from 0.1 to 20 and preferably from 0.2–10 [l/l.h].

The regeneration of the partially coked catalyst by passing an oxygen-containing gas, e.g., oxygen, thereover, likewise takes place in the presence of steam. In the simplest case, only the olefin metered feed need be interrupted. The reactor is rendered inert by further passing steam therethrough, the pressure being maintained during this step. The oxygen-containing gas is then admixed until the catalyst is cleaned by burn-off. The time needed for regeneration is 0.5–5 h. The temperature range from 450°–550° C. The oxygen-containing gas, needed for the regeneration, is in the range from 10–125% by weight and the steam from 10–100% by weight. The pressure is in the range from 1.1–10 bar. Normally it is the same range as the reaction pressure. After again rendering the reactor inert by passing pure steam in, olefin is fed once more in metered amounts. It is advantageous, prior to the metered feeding of the olefin, especially when the catalyst has just been freshly filled, to treat the catalyst for a certain time (e.g., 0.25–2 hours) only with steam. Using this procedure, flushing with a separate inert gas becomes unnecessary; thus, the number of necessary switching and regulating processes is markedly reduced.

A further advantage resides in the high heat conductivity of the steam. As a result, the heat of reaction of the burn-off step is more readily removed, avoiding the occurrence of extensive hot spots. At the same time, the burn-off velocity can be increased leading to shorter regenerating times and, thus, a better utilization of the plant.

The catalyst has the same activity and selectivity after each regeneration. The proved catalyst life time is beyond two years. Because 1.5 to 3.5 kg n-alkene can be charged per kg catalyst and hour during the whole catalyst life time between 24.000 kg and 56.000 kg n-alkene can be charged per kg catalyst.

When using mixtures with a large amount of alkene-1, for example butene-1, or a lot of cis-alkene-2, e.g., cis-butene-2, it is advantageous to have the skeleton isomerization of this invention preceded by a double-bond isomerization according to conventional methods. (See, e.g., F. Asinger "Chemie and Technologie der Monoolefine", Akademieverlag Berlin, 1957, p. 834 ff.; BE-PSS 636 484, 667 654, U.S. Pat. No. 3,642,933; whose disclosure is incorporated by reference herein.) This lowers the heat evolution in the catalyst bed, so that temperature peaks due to nonuniform heat evolution in the catalyst bed are avoided, enabling an approximately isothermal course of the reaction. All conditions of the isomerization and catalyst regeneration processes of this invention are fully conventional unless otherwise noted herein, and are given, e.g., in the following reference whose disclosures are incorporated by reference herein. B. Notari, V. Fattore, G. Manare "Scelital Isomerization of Olefins", 1980 NRPA Meeting, March, 23–25 1980, New Orleans, Louisiana; V. R. Shoudhary, L. K. Doriswany "Ind. Eng. Chem. Process Des. Development", Vol. 14, No. 3 1975, p, 227;

A particular advantage of the process is that, when operating under superatmospheric pressure, preferably with relatively large amounts of water, it is possible to avoid the use of otherwise necessary gas compressors for the recompression to the liquid state (after isomerization), since, for example, the $C_4$-alkenes are industrially available already in liquid form under pressure and are used in this form, such as, for example in the manufacture of MTB (methyl tert-butyl ether).

The isoalkenes, produced by the process of this invention, for example isobutene, are fully conventionally utilized, e.g., for the production of valuable fuel components, as well as for the manufacture of methyl methacrylate.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

COMPARATIVE EXAMPLES 1 AND 2

A fluorinated aluminum oxide catalyst is prepared by a conventional process, wherein $\eta$-$Al_2O_3$ is made into a slurry with aqueous ammonium fluoride solution, dried, and calcined at 400°–500° C.

The F content of the catalyst is 0.7%. To conduct all of the subsequent experiments, 185 ml of this catalyst is placed into a fixed bed (tubular reactor having an internal diameter of 3.0 cm). The reactor is heated by an electrically heated fluidized bath.

Mechanical volumeters are utilized for the metered feeding of the $C_4$-hydrocarbon and the optionally employed inert supplemental gas. The charge is conducted under a slight initial pressure of 1.1 bar (absolute) over the catalyst bed at 450° C. The space throughput velocity, expressed as LHSV, is 1.3 l/l.h.

The product stream is passed at 10° C. through a trap system in order to remove liquid product by condensation. The composition of the gaseous products is determined by gas chromatography. The proportion of products higher than $C_5$ is determined by gravimetry.

The following definitions are set up for conducting the analysis:

$$\text{Conversion \%} = \frac{[(BT)\text{in} - (BL)\text{out}] \times 100}{(BT)\text{in}}$$

$$\text{Selectivity for Isobutene \%} = \frac{(\text{Isobutene})\text{out} \times 100}{[(BT)\text{in} - (BL)\text{out}]}$$

$$\text{Yield of Isobutene \%} = \frac{\text{Conversion \%} \times \text{Selectivity \%}}{100}$$

$$= \frac{(\text{Isobutene})\text{out} \times 100}{(BT)\text{in}}$$

$$\text{Selectivity for} <C_4 + \text{Saturated HC} = \frac{(<C_4 + \text{Saturated HC})\text{out} \times 100}{[(BT)\text{in} - (BL)\text{out}]}$$

$$\text{Selectivity for } C_5 + HC = \frac{(C_5 + HC)\text{out} \times 100}{[(BT)\text{in} - (BL)\text{out}]}$$

The above symbols have the following meanings:

$BL$ = amount of linear butenes
= trans-butene + cis-butene + butene-1

$BT$ = amount of butene employed $<C_4$ + saturated hydrocarbons (HC)
= amount of $C_1 + C_2 + C_3$ + isobutane + n-butane $C_5 + HC$ = amount of HC of more than 4 carbon atoms The symbols "in" and "out" mean respectively fed into and discharged from the reactor.

In the comparative examples as well as in Examples 1–3, butene-1 is utilized as the educt with a purity of >99.8%.

Pure butene-1 is used in Comparative Example 1. The results are shown in Table 1.

In Comparative Example 2, 30 molar percent (based on butene-1) of hydrogen is admixed to the butene-1. The results are compiled in Table 2.

EXAMPLE 1

The catalyst described in the comparative examples is utilized (pressure likewise 1.1 bar). The butene-1 is combined with 30 molar percent, corresponding to 10% by weight (based on butene-1) of water. The water is evaporated and homogenized with the butene in a static mixer upstream of the reactor. The water contains fluorine in a concentration (employed as HF) corresponding to the fluorine concentration in the aqueous phase downstream of the reactor (40 ppm by weight). The results are indicated in Table 3.

Figure 2:
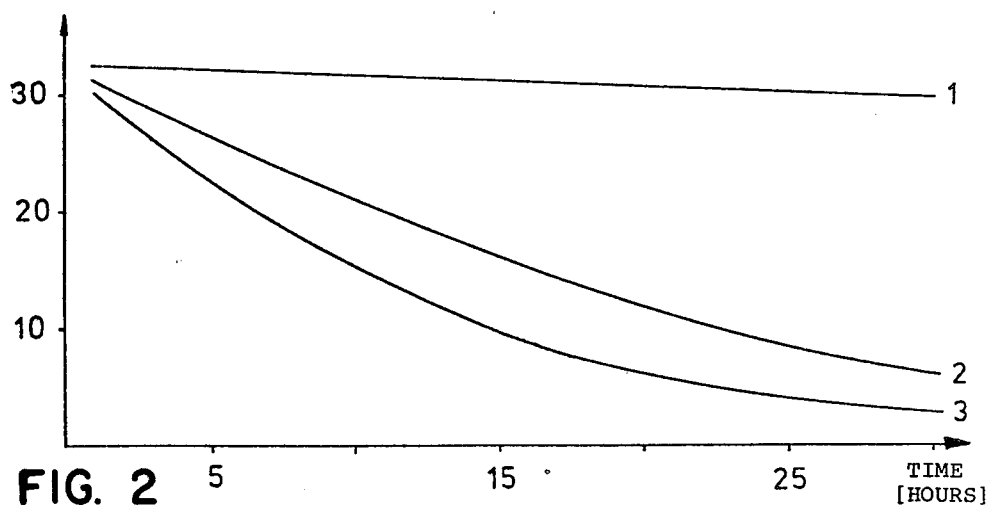
Figure 3:
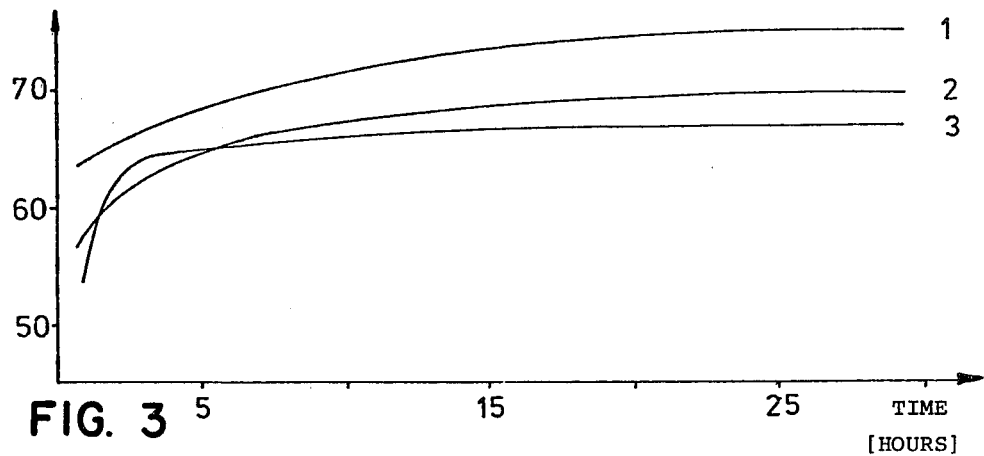

A comparison of Example 1 with the comparative examples demonstrates that when adding water to the butene-1, the deactivation of the catalyst takes place substantially more slowly. At the same time, the selectivity becomes considerably better as compared with the mode of operation without water. The advantage of adding water becomes especially apparent in the butene isomerization by FIGS. 1 through 3. In these graphic illustrations, the essential characteristic data of the reaction (conversion, isobutene selectivity, isobutene yield) are plotted as a function of the number of operating hours.

The catalyst from this example is operated under the conditions set forth therein for respectively 50 hours and then regenerated. Regeneration takes place by burning off with air (air volume 15 Nl/h; 2 hours) at the same bath temperature while retaining the metered feeding of water (F content in $H_2O$ in the form of HF: 40 ppm by weight).

The experimental results set forth in Table 4 are obtained after twelve regenerations and a total operating period (sum total of operating times between regenerations) of about 700 hours. The results show that the catalyst does not experience any damage due to the addition of water if fluorine is replenished in metered amounts in correspondence with the amounts discharged.

The same results are obtained by recirculating the water instead of replenishing fluorine in metered amounts.

COMPARATIVE EXAMPLE 1

Isomerization of Butene-1 without Addition of Inert Compounds and $H_2O$

TABLE 1

| Temperature °C. | 450 | 450 | 450 | 450 | 450 | 450 |
|---|---|---|---|---|---|---|
| Operating Hours | 1 | 2 | 6 | 8 | 20 | 30 |
| Space Velocity l/l.h | 1.3 | 1.3 | 1.3 | 1.3 | 1.3 | 1.3 |

TABLE 1-continued

| Conversion % | 54.9 | 46.7 | 31.6 | 26.2 | 10.1 | 4.0 |
|---|---|---|---|---|---|---|
| Selectivity (Isobutene) % | 54.9 | 62.2 | 65.5 | 65.9 | 66.9 | 67.4 |
| Yield (Isobutene) % | 30.1 | 29.0 | 20.7 | 17.3 | 6.7 | 2.7 |
| Selectivity ($<C_4$) % | 9.8 | 7.5 | 6.7 | 6.4 | 5.5 | 5.4 |
| Selectivity ($C_{5+}$) % | 33.4 | 28.1 | 27.5 | 27.0 | 25.8 | 25.1 |

COMPARATIVE EXAMPLE 2

Isomerization of Butene-1 with Addition of 30 Molar Percent $H_2$, But without $H_2O$

TABLE 2

| Temperature °C. | 450 | 450 | 450 | 450 | 450 | 450 |
|---|---|---|---|---|---|---|
| Operating Hours | 1 | 2 | 6 | 8 | 20 | 30 |
| Space Velocity l/l.h | 1.3 | 1.3 | 1.3 | 1.3 | 1.3 | 1.3 |
| Conversion % | 53.8 | 49.7 | 38.6 | 34.2 | 17.1 | 8.3 |
| Selectivity (Isobutene) % | 57.6 | 60.3 | 65.9 | 66.6 | 69.5 | 70.0 |
| Yield (Isobutene) % | 31.0 | 30.0 | 25.4 | 22.8 | 11.9 | 5.8 |
| Selectivity ($<C_4$) % | 10.1 | 7.4 | 6.2 | 6.0 | 5.1 | 5.0 |
| Selectivity ($C_{5+}$) % | 30.3 | 30.1 | 25.2 | 25.0 | 23.2 | 22.8 |

EXAMPLE 1

Isomerization of Butene-1 with Addition of 30 Molar Percent $H_2O$ Corresponding to 10% by Weight

TABLE 3

| Temperature °C. | 450 | 450 | 450 | 450 | 450 | 450 |
|---|---|---|---|---|---|---|
| Operating Hours | 1 | 2 | 6 | 8 | 20 | 30 |
| Space Velocity l/l.h | 1.3 | 1.3 | 1.3 | 1.3 | 1.3 | 1.3 |
| Conversion % | 51.0 | 49.7 | 48.2 | 47.3 | 41.1 | 38.9 |
| Selectivity (Isobutene) % | 63.8 | 64.9 | 68.8 | 70.4 | 74.1 | 75.0 |
| Yield (Isobutene) % | 32.5 | 32.3 | 33.1 | 33.2 | 30.5 | 29.2 |
| Selectivity ($<C_4$) % | 9.6 | 8.8 | 8.4 | 8.0 | 7.1 | 7.1 |
| Selectivity ($C_{5+}$) % | 25.8 | 25.3 | 21.9 | 20.5 | 17.0 | 16.5 |

EXAMPLE 1

Isomerization of Butene-1 with Addition of 30 Molar Percent $H_2O$ Corresponding to 10% by Weight, After 12 Regenerations

TABLE 4

| Temperature °C. | 450 | 450 | 450 | 450 | 450 |
|---|---|---|---|---|---|
| Operating Hours | 1 | 2 | 8 | 20 | 32 |
| Space Velocity l/l.h | 1.3 | 1.3 | 1.3 | 1.3 | 1.3 |
| Conversion % | 50.4 | 49.4 | 47.0 | 41.2 | 38.6 |
| Selectivity (Isobutene) % | 64.4 | 65.4 | 71.1 | 76.9 | 77.0 |
| Yield (Isobutene) % | 32.5 | 32.3 | 33.4 | 31.7 | 29.7 |
| Selectivity ($<C_4$) % | 9.8 | 8.7 | 8.0 | 7.0 | 7.0 |
| Selectivity ($C_{5+}$) % | 23.9 | 23.8 | 18.9 | 14.6 | 14.0 |

EXAMPLE 2

The catalyst used previously in Example 1 is further utilized under the conditions described therein, the water of reaction being recirculated. After eight regenerations and a total operating period of 400 hours, the catalyst shows no damage. The same results are obtained as in Example 1.

EXAMPLE 3

The catalyst as employed in Example 2 is operated under the conditions set forth therein, adding fresh water (without fluorine) and compensating for the discharged fluorine by adding a corresponding amount of tetrafluoromethane (44 ppm=44 mg $CF_4$/l $H_2O$). For metered feeding purposes, respectively 180 mg of $CF_4$ is dissolved in 40 kg of butene-1. After eight regenerations and a total operating period of 400 hours, the same results are obtained as in Example 1.

EXAMPLE 4

The catalyst already employed in Example 3 is operated under the conditions indicated in Example 1, using instead of butene-1 a $C_4$-cut having the following composition:
isobutane—7.31% by weight
n-butane—23.43% by weight
butene-1—43.92% by weight
trans-butene-2—15.50% by weight
cis-butene-2—9.80% by weight According to the results of the test, the butanes show a behavior like inert compounds. The conversion and selectivities based on butenes utilized (see Table 5) correspond essentially to the tests with pure butene-1.

EXAMPLE 4

Isomerization of a $C_4$-Cut with Addition of 10% by Weight $H_2O$

TABLE 5

| Temperature °C. | 450 | 450 | 450 | 450 | 450 |
|---|---|---|---|---|---|
| Operating Hours | 1 | 2 | 8 | 20 | 30 |
| Space Velocity l/l.h | 1.3 | 1.3 | 1.3 | 1.3 | 1.3 |
| Conversion % | 49.6 | 48.9 | 46.6 | 38.6 | 35.8 |
| Selectivity (Isobutene) % | 68.7 | 68.7 | 72.9 | 76.8 | 79.8 |
| Yield (Isobutene) % | 34.0 | 33.6 | 33.9 | 29.6 | 28.6 |
| Selectivity ($<C_4$) % | 9.6 | 9.3 | 8.2 | 7.3 | 7.0 |
| Selectivity ($C_{5+}$) % | 21.1 | 20.2 | 17.9 | 13.8 | 12.9 |

EXAMPLE 5

The catalyst described in Examples 1–4 is employed (pressure 6.0 bar). The butene-1 is combined with 400 molar percent, corresponding to 129% by weight (based on butene-1) of water. The water is evaporated and homogenized with the butene in a static mixer upstream of the reactor. The water contains fluorine in a concentration (used as HF) corresponding to the fluorine concentration in the aqueous phase downstream of the reactor (90 ppm by weight). This is achieved by the metered feeding of 0.215 ml HF 40%/l $H_2O$. The results are shown in Table 6.

The catalyst from this example is operated for 100 hours under the conditions described therein and then regenerated. Regeneration takes place by burning off with air (air volume 15 Nl/h; 2 hours) at the same bath temperature while continuing the metered feeding of water (F content in $H_2O$ as HF: 90 ppm by weight). The evolution of heat during regeneration ceased after a matter of minutes.

The test results in Table 7 are obtained after twelve regenerations and a total operating time (sum total of the operating periods between regenerations) of about 1000 hours. The results demonstrate that the catalyst is not damaged by the addition of water, if fluorine is added in metered amounts in correspondence with the discharged quantity.

The same results are obtained by recirculating the water instead of adding fluorine in metered amounts.

EXAMPLE 5

Isomerization of Butene-1 at 6 Bar with Addition of 400 Molar Percent of Water Corresponding to 129% by Weight

TABLE 6

| Temperature °C. | 450 | 450 | 450 | 450 | 450 |
|---|---|---|---|---|---|
| Operating Hours | 1 | 2 | 24 | 45 | 100 |
| Space Velocity l/l.h | 1.3 | 1.3 | 1.3 | 1.3 | 1.3 |

TABLE 6-continued

| | | | | | |
|---|---|---|---|---|---|
| Conversion % | 17.4 | 18.1 | 19.1 | 19.3 | 19.0 |
| Selectivity (Isobutene) % | 94.1 | 93.2 | 94.1 | 93.3 | 93.0 |
| Yield (Isobutene) % | 16.4 | 16.9 | 18.0 | 18.0 | 17.7 |
| Selectivity (<$C_4$) % | 2.9 | 3.8 | 3.3 | 3.6 | 3.8 |
| Selectivity ($C_{5+}$) % | 2.9 | 2.7 | 2.5 | 2.6 | 2.5 |

TABLE 7

| | | | | |
|---|---|---|---|---|
| Temperature °C. | 450 | 450 | 450 | 450 |
| Operating Hours | 1 | 2 | 20 | 51 |
| Space Velocity l/l.h | 1.3 | 1.3 | 1.3 | 1.3 |
| Conversion % | 18.0 | 18.2 | 19.0 | 19.2 |
| Selectivity (Isobutene) % | 93.0 | 93.1 | 93.5 | 93.3 |
| Yield (Isobutene) % | 16.7 | 16.9 | 17.8 | 18.0 |
| Selectivity (<$C_4$) % | 3.5 | 3.8 | 4.0 | 3.9 |
| Selectivity ($C_{5+}$) % | 2.4 | 2.5 | 2.3 | 2.4 |

EXAMPLE 6

Butene-1 is reacted together with 300 molar percent, corresponding to 96% by weight (based on butene-1) of water in accordance with the description of Example 5, but at 460° C. and with a space throughput velocity of 1.1 l/l.h. The conversion—based on butenes employed—and the selectivity are listed in Table 8.

The regeneration of the catalyst conducted under 6 bar and at a bath temperature of 460° C. with air (15 Nl/h) and fluoride-containing steam (118 ml $H_2O$ liquid, F content in $H_2O$ as HF: 90 ppm by weight) was terminated after 120 minutes (end of heat evolution).

EXAMPLE 6

Isomerization of Butene-1 at 6 Bar with Addition of 300 Molar Percent of Water Corresponding to 96% by Weight

TABLE 8

| | | | | | | |
|---|---|---|---|---|---|---|
| Temperature °C. | 460 | 460 | 460 | 460 | 460 | 460 |
| Operating Hours | 1 | 2 | 17 | 25 | 50 | 100 |
| Space Velocity l/l.h | 1.1 | 1.1 | 1.1 | 1.1 | 1.1 | 1.1 |
| Conversion % | 35.1 | 30.0 | 26.5 | 25.7 | 25.0 | 22.9 |
| Selectivity (Isobutene) % | 73.1 | 78.0 | 82.7 | 83.4 | 87.0 | 87.1 |
| Yield (Isobutene) % | 25.7 | 23.4 | 22.0 | 21.4 | 21.8 | 20.0 |
| Selectivity (<$C_4$) % | 8.5 | 6.8 | 5.4 | 5.1 | 4.8 | 4.9 |
| Selectivity ($C_{5+}$) % | 17.7 | 15.1 | 11.3 | 11.0 | 7.7 | 7.3 |

EXAMPLE 7

According to the directions of Example 6, butene-1 is conducted in a mixture with 64% by weight of $H_2O$ over the freshly regenerated catalyst under a total pressure of 6 bar but at 470° C. and an increased residence time (space throughput velocity 1.1 l/l.h). Conversion (based on butenes employed) and selectivity are obtained as set forth in Table 9. The regenerating period for the catalyst (corresponding to regenerating period/butene load . duration of test) amounts to twice the time required in Example 6.

EXAMPLE 7

Isomerization of Butene-1 to 6 Bar with Addition of 200 Molar Percent of Water Corresponding to 64% by Weight

TABLE 9

| | | | | | | |
|---|---|---|---|---|---|---|
| Temperature °C. | 470 | 470 | 470 | 470 | 470 | 470 |
| Operating Hours | 1 | 2 | 17 | 21 | 49 | 100 |
| Space Velocity l/l.h | 1.1 | 1.1 | 1.1 | 1.1 | 1.1 | 1.1 |
| Conversion % | 43.1 | 40.1 | 35.5 | 33.8 | 31.0 | 26.1 |
| Selectivity (Isobutene) % | 64.0 | 67.1 | 71.0 | 74.0 | 74.5 | 74.7 |
| Yield (Isobutene) % | 27.6 | 26.9 | 25.2 | 25.0 | 23.1 | 19.5 |
| Selectivity (<$C_4$) % | 9.4 | 8.1 | 7.3 | 7.5 | 8.5 | 8.2 |
| Selectivity ($C_{5+}$) % | 25.7 | 24.8 | 21.0 | 18.5 | 16.8 | 16.3 |

EXAMPLE 8

According to the description in Example 6, 1.3 l/l.h of a mixture of linear butenes (recovered from isomerization tests after complete removal of the isobutene by MTB formation; composition 26.5% butene-1, 41.5% trans-butene, 31.0% cis-butene; minor amounts of $C_5$- as well as saturated $C_4$-HC) is reacted in a mixture with 200 molar percent of water (64% by weight) on a freshly regenerated catalyst. Conversion and selectivity are as set forth in Table 10. The regeneration of the catalyst takes a time period which is smaller by the factor 0.7 with the same isomerization period as well as a comparable yield of isobutene as in Example 7. This result, as well as the improved selectivity, are due to the fact that with the use of butene mixtures in place of butene-1 a uniform temperature profile is obtained over the reactor and thus the catalyst utilization is more optimal, with a reduced coke formation due to the avoidance of temperature peaks.

EXAMPLE 8

Isomerization of an n-Butene Equilibrium Mixture at 6 Bar with Addition of 200 Molar Percent of Water Corresponding to 64% by Weight

TABLE 10

| | | | | | |
|---|---|---|---|---|---|
| Temperature °C. | 475 | 475 | 475 | 475 | 475 |
| Operating Hours | 1 | 2 | 25 | 50 | 100 |
| Space Velocity l/l.h | 1.3 | 1.3 | 1.3 | 1.3 | 1.3 |
| Conversion % | 35.0 | 30.1 | 28.3 | 26.5 | 23.9 |
| Selectivity (Isobutene) % | 70.1 | 72.3 | 77.7 | 79.6 | 82.9 |
| Yield (Isobutene) % | 24.5 | 24.0 | 22.0 | 21.1 | 19.7 |
| Selectivity (<$C_4$) % | 5.2 | 5.3 | 4.9 | 4.6 | 3.5 |
| Selectivity ($C_{5+}$) % | 23.9 | 21.8 | 16.5 | 14.6 | 13.8 |

EXAMPLE 9

According to the data of Example 6, cis-transbutene (cis/trans ratio 27:73) is reacted on a freshly regenerated catalyst with a space throughput velocity of 1.3 l/l.h at 6.0 bar and 470° C. in a mixture with steam (170 molar percent, corresponding to 55% by weight, based on butene-2). Conversion and selectivity are set forth in Table 11. The regeneration, conducted under 6 bar and at a bath temperature of 470° C. with 15 Nl/h of air and the same water charge as in the isomerization was ended after 5.5 hours.

EXAMPLE 10

With a space throughput velocity of 1.3 l/l.h, cis-butene is reacted together with 435 molar percent, corresponding to 140% by weight of water according to the description of Example 6 at 480° C. Constant conversions and selectivities are obtained as set forth in Table 12. The regeneration of the catalyst, conducted under 6 bar and at a bath temperature of 480° C. with air (15 Nl/h) and 215 ml of $H_2O$ (fluoride-containing steam; F content in $H_2O$ as HF: 90 ppm by weight) was terminated after a few minutes. This proves the fact that deactivation by coke formation is practically nonexistent under the advantageous conditions of large additions of water.

EXAMPLE 9

Isomerization of cis-/trans-Butene-2 at 6 Bar with Addition of 170 Molar Percent of Water Corresponding to 55% by Weight

TABLE 11

| Temperature °C. | 470 | 470 | 470 | 470 | 470 | 470 |
|---|---|---|---|---|---|---|
| Operating Hours | 1 | 2 | 25 | 40 | 58 | 100 |
| Space Velocity l/l.h | 1.3 | 1.3 | 1.3 | 1.3 | 1.3 | 1.3 |
| Conversion % | 37.5 | 35.2 | 27.1 | 25.2 | 23.9 | 20.9 |
| Selectivity (Isobutene) % | 65.3 | 68.5 | 73.5 | 74.6 | 76.4 | 82.7 |
| Yield (Isobutene) % | 24.5 | 24.1 | 19.9 | 19.8 | 18.3 | 17.3 |
| Selectivity ($<C_4$) % | 6.6 | 5.8 | 2.9 | 2.6 | 2.8 | 2.5 |
| Selectivity ($C_{5+}$) % | 27.4 | 25.3 | 23.2 | 22.4 | 20.4 | 14.2 |

EXAMPLE 10

Isomerization of cis-Butene-2 at 6.0 Bar with Addition of 435 Molar Percent of Water Corresponding to 140% by Weight

TABLE 12

| Temperature °C. | 480 | 480 | 480 | 480 | 480 |
|---|---|---|---|---|---|
| Operating Hours | 1 | 2 | 15 | 30 | 50 |
| Space Velocity l/l · h | 1.3 | 1.3 | 1.3 | 1.3 | 1.3 |
| Conversion % | 19.1 | 18.9 | 18.4 | 18.1 | 18.0 |
| Selectivity (Isobutene) % | 89.2 | 90.3 | 90.5 | 91.2 | 91.0 |
| Yield (Isobutene) % | 17.0 | 17.1 | 16.7 | 16.5 | 16.4 |
| Selectivity ($<C_4$) % | 2.0 | 1.8 | 1.4 | 0.8 | 1.2 |
| Selectivity ($C_{5+}$) % | 7.9 | 7.5 | 7.3 | 7.6 | 6.9 |

EXAMPLE 11

On the catalyst employed in Example 1 (185 ml in a tubular reactor having a diameter of 3.0 cm; heated with electrical fluidized bath), 1.1 l/l.h of 1-pentene (>99%) is reacted under a pressure of 1.1 bar and at a temperature of 440° C. in a mixture with steam (387 g/l.h, corresponding to 55% by weight, based on pentene). The water contains fluorine in a concentration (used as HF) of 90 ppm by weight. The product stream is conducted at 15° C. through a trap system to remove liquid product by condensation. The composition of the gaseous products and of the $C_5$-products is determined by gas chromatography. The proportion of the products higher than $C_5$ is determined by gravimetry after removing the $C_5$-proportions by distillation. To conduct the analysis, the following definitions are drawn up:

$$\text{Conversion \%} = \frac{[(\Sigma PL)\text{in} - (\Sigma PL)\text{out}] \times 100}{(\Sigma PL)\text{in}}$$

$$\text{Selectivity for Isopentene \%} = \frac{(\Sigma IP)\text{out} \times 100}{[(\Sigma PL)\text{in} - (\Sigma PL)\text{out}]}$$

$$\text{Yield of Isopentenes \%} = \frac{\text{Conversion \%} \times \text{Selectivity \%}}{100}$$

$$= \frac{(\Sigma IP)\text{out} \times 100}{(\Sigma PL)\text{in}}$$

$$\text{Selectivity for } <C_5 + \text{Saturated HC} = \frac{(<C_5 + \text{Saturated HC})\text{out} \times 100}{[(PL)\text{in} - (PL)\text{out}]}$$

$$\text{Selectivity for } C_6 + HC = \frac{(C_6 + HC)\text{out} \times 100}{[(PL)\text{in} - (PL)\text{out}]}$$

The above symbols have the following meanings:

$\Sigma PL$ = sum total of linear pentenes
    = 1-pentene + cis-2-pentene + trans-2-pentene $\Sigma IP$ = sum total of branched pentenes
    = 2-methyl-1-butene + 2-methyl-1-butene + 3-methyl-1-butene $<C_5$ + Saturated Hydrocarbons (HC)
    = amount of $C_1 + C_2 + C_3 + C_4$ + isopentane + n-pentane $C_6$ + HC = amount of HC of more than 5 carbon atoms The symbols "in" and "out" mean introduced into and discharged from the reactor.

The product obtained in accordance with Table 13 contains, in addition to linear pentenes, isopentenes, as well as a minor proportion of cracked products, saturated products, and $C_{6+}$ products. The use of large amounts of water permits a high selectivity for isoamylenes, representing important chemical raw materials, e.g. for the manufacture of amylphenols, octane-number-improving ethers, and isoamyl alcohol.

EXAMPLE 11

Isomerization of 1-Pentene at 1.1 Bar with Addition of 214 Molar Percent of Water Corresponding to 55% by Weight

TABLE 13

| Temperature °C. | 440 | 440 | 440 | 440 | 440 |
|---|---|---|---|---|---|
| Operating Hours | 1 | 2 | 8 | 20 | 30 |
| Space Velocity l/l · h | 1.1 | 1.1 | 1.1 | 1.1 | 1.1 |
| Conversion % | 30.4 | 29.9 | 28.7 | 27.8 | 27.2 |
| Selectivity (Isopentenes) % | 88.2 | 88.7 | 89.8 | 90.5 | 91.0 |
| Yield (Isopentenes) % | 26.8 | 26.5 | 25.8 | 25.2 | 24.7 |
| Selectivity ($<C_5$) % | 4.2 | 4.0 | 3.5 | 3.4 | 2.8 |
| Selectivity ($C_{6+}$) % | 8.0 | 7.8 | 7.1 | 6.5 | 6.3 |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the catalytic skeleton isomerization of an n-alkene to an isoalkene comprising contacting the n-alkene with a fluorinated aluminum oxide catalyst at a temperature of 250°–550° C., in the presence of 0.5–150% by weight of water, based on the amount of alkene employed.

2. A process of claim 1 wherein the amount of water employed is 2–130% by weight.

3. A process of claim 1 wherein the n-alkene is a butene or a mixture thereof with other hydrocarbon components.

4. A process of claim 1 wherein the reaction is conducted under superatmospheric pressure.

5. A process of claim 1 wherein the fluorine emanating from the isomerization reaction is replenished during the course of the reaction on a continuous or discontinuous basis.

6. A process of claim 5 wherein the fluorine is replenished by adding corresponding metered amounts of HF to the water component of the reaction.

7. A process of claim 6 which is carried out continuously.

8. A process of claim 5 wherein the fluorine is replenished by addition of a volatile fluorine compound to the reaction.

9. A process of claim 5 wherein the fluorine replenishment is effected by recirculating the reaction water containing the fluorine effluent.

10. A process of claim 1 or 5 further comprising regenerating the fluorinated aluminum oxide catalyst, after it has been partially deactivated due to coking effects, by burning it off with an $O_2$- containing gas in the presence of steam.

11. A process of claim 10, wherein the alkene is isomerized at 1-10 bar and the catalyst is regenerated under pressure.

12. A process of claim 11 wherein the isomerization pressure is 3-7 bar.

13. A process of claim 1 wherein the n-alkene is a $C_{4-16}$-alkene.

* * * * *